United States Patent
Müller; Klaus-Helmut

Patent Number: 5,463,138
Date of Patent: Oct. 31, 1995

[54] PROCESS FOR PREPARING DIFLUOROMETHOXYARENES AND DIFLUOROMETHYLTHIOARENES

[75] Inventor: Klaus-Helmut Müller, Düsseldorf, Germany

[73] Assignee: Bayer Aktiengesellschaft, Leverkusen, Germany

[21] Appl. No.: 245,330

[22] Filed: May 18, 1994

[30] Foreign Application Priority Data

May 25, 1993 [DE] Germany .......................... 43 17 322.5

[51] Int. Cl.[6] .................................... C07C 41/01
[52] U.S. Cl. .................... 568/655; 568/38; 568/42; 568/43; 568/54; 568/56; 568/337; 568/588; 568/649; 568/656
[58] Field of Search .................... 568/43, 56, 655, 568/38, 42, 54, 337, 588, 649, 656

[56] References Cited

U.S. PATENT DOCUMENTS

| | | | |
|---|---|---|---|
| 4,404,148 | 9/1983 | Siddens | 568/655 |
| 4,405,529 | 9/1983 | Siddens et al. | 568/655 |
| 4,407,760 | 10/1983 | Siddens | 568/655 |
| 4,595,763 | 6/1986 | Renga et al. | 568/655 |
| 4,816,596 | 3/1989 | Langlois | 568/655 |
| 5,105,021 | 4/1992 | Akieda et al. | 568/655 |

FOREIGN PATENT DOCUMENTS

101570  7/1983  European Pat. Off. ............. 568/56

OTHER PUBLICATIONS

Fieser's General Textbook, vol. 12, p. 329 (1987).
James M. Renga, et al, "The Salt free Synthesis of Aryl Ethers Using Methyl Trichloracetate", Syn. Comm. vol. 14(1) pp. 69–76 (1984).
Chemical Abstracts, vol. 115, No. 25, 23, Dec. 1991 Abstract No. 279585f.
Chemical Abstracts, vol. 113, No. 13, Sep. 1985 Abstract No. 104979n.
J. Org. Chem. vol. 25, pp. 2009–2012 (1960).
Chem. Abstracts vol. 70: 96318d (1969).
Bull. Soc. Chim. Belg. vol. 74, pp. 270–280 (1965).
Chem. Abstracts vol. 102: 78548d (1985).
J. Fluorine Chem. vol. 41, pp. 247–261 (1988).

*Primary Examiner*—James H. Reamer
*Attorney, Agent, or Firm*—Sprung Horn Kramer & Woods

[57] ABSTRACT

Difluoromethoxyarenes and difluoromethylthioarenes of the general formula (I), $$Ar-Q-CHF_2 \qquad (I)$$

in which
  Ar represents optionally substituted aryl, and
  Q represents oxygen or sulphur,
(which can be used as intermediates for preparing biologically active products) are obtained in very good yields and in a high degree of purity by reacting hydroxyarenes or mercaptoarenes of the general formula $$Ar-Q-H \qquad (II)$$

with chlorodifluoromethane ($ClCHF_2$) in the presence of an aqueous alkali metal hydroxide or alkaline earth metal hydroxide at temperatures of between 20° C. and 120° C., the reaction being carried out in the presence of a phase-transfer catalyst from the group comprising the tetrasubstituted ammonium salts and phosphonium salts, and in the presence of a non-polar or moderately polar solvent from the group comprising the aliphatic or alicyclic hydrocarbons or from the group comprising the aromatic hydrocarbons, which are optionally substituted by chlorine, or from the group comprising the branched alkyl ethers.

11 Claims, No Drawings

PROCESS FOR PREPARING DIFLUOROMETHOXYARENES AND DIFLUOROMETHYLTHIOARENES

The invention relates to a novel process for preparing difluoromethoxyarenes and difluoromethylthioarenes, which can be used as intermediates for preparing biologically active products.

It is known that difluoromethoxyarenes or difluoromethylthioarenes are obtained if hydroxyarenes or mercaptoarenes, respectively, are reacted with chlorodifluoromethane in the presence of sodium hydroxide and using dioxane as the diluent (cf. J. Org. Chem. 25 (1960), 2009–2012; Zh. Obshch. Khim. 39 (1969), 206–210—cited in Chem. Abstracts 70:96318d; Bull. Soc. Chim. Belg. 74 (1965), 270–280).

However, only unsatisfactory yields are sometimes achieved when this synthesis method is employed. In addition, the use of dioxane for industrial applications involves disposal problems and the risks associated with the formation of peroxides.

It is furthermore known that the reaction of hydroxyarenes with chlorodifluoromethane in the presence of sodium hydroxide can also be carried out using acetone/water or acetone/isopropanol/water as diluents, optionally in the presence of a phase-transfer catalyst, such as, for example, benzyltriethylammonium chloride, and optionally under elevated pressure (cf. EP-A 101570, U.S. Pat. No. 4,404, 148, U.S. Pat. No. 4,405,529, U.S. Pat. No. 4,407,760).

The yield and quality of the products are not entirely satisfactory in this procedure either.

It is additionally known that difluoromethoxyarenes can be obtained in good yields by reacting hydroxyarenes with chlorodifluoromethane in the presence of bases and using highly polar, aprotic solvents (cf. JP-A 59157041—cited in Chem. Abstracts 102:78548d).

If at all possible, however, the use of highly polar, aprotic solvents on an industrial scale should be avoided on account of the ecological problems which are associated with them.

It is known, finally, that difluoromethoxyarenes and difluoromethylthioarenes can also be obtained by reacting corresponding hydroxyarenes or mercaptoarenes with chlorodifluoromethane in moderately polar, aprotic solvents using solid sodium hydroxide in the presence of tris-(3,6-dioxaheptyl)-amine (cf. J. Fluorine Chem. 41 (1988), 247–261).

Under these conditions, too, the desired products are often obtained in yields and of a quality which are unsatisfactory.

It has now been found that difluoromethoxyarenes or difluoromethylthioarenes of the general formula (I)

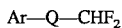

$$Ar\text{---}Q\text{---}CHF_2 \qquad (I)$$

in which

Ar represents optionally substituted aryl, and

Q represents oxygen or sulphur, are obtained in very good yields and at high purity if hydroxyarenes or mercaptoarenes of the general formula (II)

$$Ar\text{---}Q\text{---}H \qquad (II)$$

in which

Ar and Q have the abovementioned meaning,
are reacted with chlorodifluoromethane (ClCHF$_2$) in the presence of an aqueous alkali metal hydroxide or alkaline earth metal hydroxide at temperatures of between 20° C. and 120° C., the reaction being carried out in the presence of a phase-transfer catalyst from the group comprising the tetrasubstituted ammonium salts and phosphonium salts, and in the presence of a non-polar or moderately polar solvent from the group comprising the aliphatic or alicyclic hydrocarbons or the group comprising the aromatic hydrocarbons which are optionally substituted by chlorine or the group comprising the branched alkyl ethers.

Surprisingly, the compounds of the formula (I) can be obtained by the process according to the invention, in which process considerably less chlorodifluoromethane and considerably less alkali metal hydroxide or alkaline earth metal hydroxide are required as compared with the known processes, in considerably improved yields and practically free from byproducts, while the recovery of the solvents, which are practically immiscible with water, can be effected without great effort.

The process according to the invention thus represents a valuable enrichment of the state of the art.

The process according to the invention preferably relates to the preparation of difluoromethoxyarenes or difluoromethylthioarenes of the formula (I), in which Ar represents in each case optionally substituted phenyl or naphthyl, where the substituents are preferably selected from the group comprising halogen, nitro, cyano, carboxyl, carbamoyl, $C_1$–$C_4$-alkyl (which is optionally substituted by halogen, cyano, carboxyl, carbamoyl, hydroxyl, amino, $C_1$–$C_4$-alkoxy or by geminate bis-($C_1$–$C_4$-alkoxy)-groupings or by $C_1$–$C_4$-alkoxy-carbonyl or phenyl), $C_1$–$C_4$-alkoxy (which is optionally substituted by halogen, cyano, carboxyl, carbamoyl, hydroxyl, amino, $C_1$–$C_4$-alkoxy or $C_1$–$C_4$-alkoxycarbonyl), $C_1$–$C_4$-alkylthio, $C_1$–$C_4$-alkylsulphinyl or $C_1$–$C_4$-alkyl-sulphonyl (which are in each case optionally substituted by halogen), $C_1$–$C_4$-alkylamino, di-($C_1$–$C_4$-alkyl)-amino, $C_1$–$C_4$-alkyl-carbonyl, $C_1$–$C_4$- alkoxy-carbonyl, $C_1$–$C_4$-alkylamino-carbonyl, di-($C_1$–$C_4$-alkyl) -amino-carbonyl, $C_1$–$C_4$-alkylcarbonyloxy, $C_1$–$C_4$-alkyl-carbonyl amino, $C_1$–$C_4$-alkoxy-carbonyloxy, $C_1$–$C_4$-alkoxy-carbonylamino, $C_1$–$C_4$-alkylamino-carbonyloxy or $C_1$–$C_4$-alkylamino-carbonylamino (which are in each case optionally substituted by halogen or $C_1$–$C_4$-alkoxy), phenyl, phenoxy, phenylthio, phenylsulphinyl, phenylsulphonyl, phenylamino, phenylcarbonyl, phenylazo or phenylazoxy (which in each case optionally contain substituents, as they are indicated above by way of example), and Q represents oxygen or sulphur.

The process according to the invention relates, in particular, to the preparation of difluoromethoxyarenes or difluoromethylthioarenes of the formula (I), in which Ar represents in each case optionally substituted phenyl or naphthyl, where the substituents are preferably selected from the group comprising fluorine, chlorine, bromine, nitro, cyano, carboxyl, carbamoyl, methyl, ethyl, n- or i-propyl (which are in each case optionally substituted by fluorine, chlorine, cyano, carboxyl, hydroxyl, methoxy, ethoxy, methoxycarbonyl, ethoxycarbonyl or phenyl), methoxy, ethoxy, n- or i-propoxy (which are in each case optionally substituted by fluorine, chlorine, cyano, carboxyl, hydroxyl, methoxy, ethoxy, methoxycarbonyl or ethoxycarbonyl), methylthio, ethylthio, methylsulphinyl, ethylsulphinyl, methylsulphonyl or ethylsulphonyl (which are in each case optionally substituted by fluorine or chlorine), methylamino, ethylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acetyloxy, propionyloxy, acetylamino, propionylamino, methoxycarbonyloxy, ethoxycarbonyloxy, methoxycarbonylamino, ethoxycarbonylamino, methylaminocarbonyloxy, ethylaminocarbonyloxy, methylaminocarbonylamino or ethylaminocarbonylamino (which are in each case optionally substituted by fluorine, chlorine, methoxy or ethoxy), phenyl, phenoxy, phenylthio, phenylsulphinyl, phenylsulphonyl, phenylamino or phenylcarbonyl (which in each case optionally contain substituents, as they are indicated above by way of example), and Q represents oxygen or sulphur.

In the case where, in formula (I), the radical Ar contains alkyl substituted by alkoxy, geminate bis-alkoxyalkyl radicals are also expressly included in the definitions (i.e. aldehyde acetals and ketone acetals).

Examples which may be mentioned of the compounds which can be prepared particularly successfully by the process according to the invention are: 1-difluoromethoxy-2-nitro-benzene, 1-difluoromethoxy- 3-nitro-benzene, 1-difluoromethoxy-4-nitro-benzene and 4-difluoromethoxy-acetophenone.

If, for example, 2-fluoro-phenol and chlorodifluoromethane are used as the starting compounds, the course of the reaction in the process according to the invention can then be diagrammatically represented by the following formula scheme:

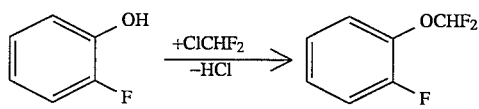

The hydroxyarenes or mercaptoarenes which are to be used as starting compounds in the process according to the invention are defined generally by the formula (II). In the formula (II), Ar and Q preferably or in particular have those meanings which have already been indicated above, in connection with the description of the compounds of the formula (I) which are to be prepared in accordance with the invention, as being preferable or particularly preferred for Ar and Q.

Examples of the starting compounds of the formula (II) which may be mentioned are: 2-nitro-phenol, 3-nitro-phenol, 4-nitro-phenol and 4-hydroxy-acetophenone.

The starting compounds of the formula (II) are—as is the chlorodifluoromethane which is also required as a starting compound—known organic chemicals.

The process according to the invention is carried out using an alkali metal hydroxide or alkaline earth metal hydroxide.

Examples of suitable alkali metal hydroxides and alkaline earth metal hydroxides which may be mentioned are: lithium hydroxide, sodium hydroxide, potassium hydroxide, magnesium hydroxide and calcium hydroxide. Sodium hydroxide is particularly preferred.

The process according to the invention is carried out using a phase-transfer catalyst from the group comprising the tetrasubstituted ammonium salts and phosphonium salts (halides, hydroxides, hydrogen sulphates, tetrafluoroborates, etc.).

Examples of such catalysts which may be mentioned are: tetrabutylammonium bromide, tetrabutylammonium chloride, tetraoctylammonium chloride, tetrabutylammonium hydrogen sulphate, methyl-trioctylammonium chloride, hexadecyltrimethylammonium chloride, hexadecyl-trimethylammonium bromide, benzyltrimethyl-ammonium chloride, benzyltriethylammonium chloride, benzyl-trimethylammonium hydroxide, benzyl-triethylammonium hydroxide, benzyltributylammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide and tetraphenylphosphonium bromide. These phase-transfer catalysts are commercially available chemicals. The process according to the invention is carried out using a non-polar or moderately polar solvent from the group comprising the aliphatic or alicyclic hydrocarbons or from the group comprising the aromatic hydrocarbons, which are optionally substituted by chlorine, or from the group comprising the branched alkyl ethers. Examples of these solvents which may be mentioned are: pentane, hexane, heptane, octane (in each case straight-chain or branched), cyclohexane, methylcyclohexane, petroleum ether, benzine, ligroin, benzene, toluene, xylene (all the isomers), cumene, chlorobenzene, o-dichlorobenzene, diisopropyl ether, diisobutyl ether, methyl sec-butyl ether, methyl tert-butyl ether, methyl sec-pentyl ether and methyl tert-pentyl ether.

Toluene, xylene (all the isomers), methyl tert-butyl ether and methyl tert-pentyl ether are particularly preferred.

When carrying out the process according to the invention, the reaction temperatures can be varied over a relatively wide range. In general, temperatures of between 20° C. and 120° C., preferably of between 40° C. and 110° C., in particular of between 60° C. and 100° C., are employed.

For carrying out the process according to the invention, between 1 and 5 mol, preferably between 1.2 and 4.5 mol, of chlorodifluoromethane, between 1.5 and 2.5 molar equivalents, preferably between 1.8 and 2.2 molar equivalents, of alkali metal hydroxide or alkaline earth metal hydroxide, and between 1 mol % and 10 mol %, preferably between 2 mol % and 5 mol %, of phase-transfer catalyst are generally employed per 1 mol of starting compound of the formula (II).

In a preferred embodiment of the process according to the invention, the starting compound of the formula (II), the alkali metal hydroxide or alkaline earth metal hydroxide, which is dissolved or dispersed in water, the non-polar or moderately polar solvent and the phase-transfer catalyst are mixed together and chlorodifluoromethane is then passed into this mixture, at the appropriate reaction temperature and while stirring vigorously, until the reaction is complete—recognizable, for example, from the colour change.

The working up and isolation of the products of the formula (I) may be carried out in accordance with customary methods. For example, the mixture is diluted with water, the organic phase is separated off and the aqueous phase is then subsequently extracted with the particular organic solvent used. The combined organic phases are washed with water, dried with sodium sulphate and filtered. The filtrate is then concentrated in a water jet vacuum and the crude product, obtained as a residue, is then purified in accordance with customary methods (e.g. by vacuum distillation) (compare also the preparation examples).

The compounds which can be prepared in accordance with the process according to the invention may be used as intermediates for preparing biologically active products, for example herbicides (cf. DE-OS (German Published Specification) 3503773=EP-A-192 998=U.S. Pat. No. 4,769,062; also EP-A-23 422=U.S. Pat. No. 4,452,628; U.S. Pat. No. 4,534,788) or insecticides (cf. EP-A 58424, U.S. Pat. No. 4,464,386, EP-A 277091, EP-A 466408, U.S. Pat. No. 5,109,014, EP-A 490569).

PREPARATION EXAMPLES

Example 1

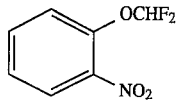

322 g (3.72 mol) of chlorodifluoromethane are passed, at 90° C., into a vigorously stirred mixture consisting of 139 g (1.0 mol) of 2-nitro-phenol, 80 g (2.0 mol) of sodium hydroxide, 120 ml of water, 1,400 ml of toluene and 16 g (0.05 mol) of tetrabutylammonium bromide.

When the colour of the reaction mixture has changed from red to light yellow, the mixture is allowed to cool down to about 20° C. and is then diluted with water to approximately twice the volume, and the organic phase is separated off. The aqueous phase is subsequently extracted a further two times with toluene. The combined organic phases are then washed with water, dried with sodium sulphate and filtered. The filtrate is concentrated in a water jet vacuum and the crude product, which remains as a residue, is purified by vacuum distillation.

177 g (94% of theory) of 1-difluoromethoxy-2-nitrobenzene are obtained with a boiling point in the region of 60° C.–62° C. (at 0.3 mbar). (Content by HPLC: 99.95%).

(cf. Zh. Obshch. Khim. 39 (1969), 206-210; yield: 80% of theory).

Example 2

In an analogous implementation to that in Example 1, the only differences being that xylene is used instead of toluene as the solvent and only 123 g (1.42 mol) of chlorodifluoromethane are expended, 170 g (content: 98.3%, i.e. 88.4% of theory) of 1-difluoromethoxy-2-nitro-benzene are obtained.

Example 3

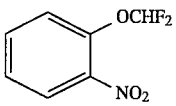

A mixture consisting of 14.0 g (0.1 tool) of 2-nitrophenol, 8.0 g (0.2 mol) of sodium hydroxide, 12 ml of water, 140 ml of methyl tert-pentyl ether and 1.6 g (0.005 mol) of tetrabutylammonium bromide is reacted with 39 g (0.45 mol) of chlorodifluoromethane as described in Example 1 and worked up in the same manner.

17.4 g (content: 99.2%; i.e. 91.3% of theory) of 1-difluoromethoxy-2-nitro-benzene are obtained.

Example 4

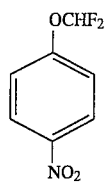

141.7 g (content: 98%; 1.0 mol) of 4-nitro-phenol are dissolved in 1,400 ml of toluene, and a 40% strength aqueous solution of sodium hydroxide is carefully added dropwise while stirring. After heating the mixture to 90° C., 17 g (0.05 mol) of tetrabutylphosphonium bromide are added to it and 150 g (1.73 mol) of chlorodifluoromethane are then passed in while stirring. Processing subsequently takes place as described under Example 1.

183.1 g (content: 100%; 96.8% of theory) of 1-difluoromethoxy- 4-nitro-benzene are obtained with a boiling point of 120° C. (at 18.6 mbar), which compound gradually crystallizes (melting point: 35° C.).

(cf. JP-A 59157041; yield: 77% of theory).

Example 5

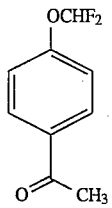

13.6 g (0.1 mot) of 4-hydroxy-acetophenone are dissolved in 140 ml of toluene, and 20 g of a 40% strength aqueous solution of sodium hydroxide and 1.6 g of tetrabutylammonium bromide are then added to this solution at 65° C. 33 g (0.38 mol) of chlorodifluoromethane are then passed in at about 90° C. while stirring vigorously. The working up is carried out as described in Example 1.

16.3 g (content: 99.6%, i.e. 87.1% of theory) of 4-difluoromethoxy-acetophenone are obtained with a boiling point in the region of 129° C.–131° C. (at 20 mbar).

(cf. J. Fluorine Chem. 41 (1988), 247–261; yield: 89%, based, however, on only 30% conversion).

It will be appreciated that the instant specification and claims are set forth by way of illustration and not limitation, and that various modifications and changes may be made without departing from the spirit and scope of the present invention.

I claim:

1. In the preparation of a difluoromethoxyarene or a difluoromethylthioarene of the formula (I)

Ar—Q—CHF$_2$ in which

Ar represents phenyl or naphthyl, each optionally substituted by at least one member selected from the group consisting of halogen, nitro, cyano, carboxyl, carbamoyl, $C_1$–$C_4$-alkyl (which is optionally substituted by halogen, cyano, carboxyl, carbamoyl, hydroxyl, amino, $C_1$–$C_4$-alkoxy or by a geminate bis-($C_1$–$C_4$-alkoxy)-grouping or by $C_1$–$C_4$-alkoxy-carbonyl or phenyl), $C_1$–$C_4$-alkoxy (which is optionally substituted by halogen, cyano, carboxyl, carbamoyl, hydroxyl, amino, $C_1$–$C_4$-alkoxy or $C_1$–$C_4$-alkoxy-carbonyl, $C_1$–$C_4$-alkylthio, $C_1$–$C_4$-alkylsulphinyl, $C_1$–$C_4$-alkylsulphonyl (each of which is optionally substituted by halogen), $C_1$–$C_4$-alkylamino, di-($C_1$–$C_4$-alkyl)-amino, $C_1$–$C_4$-alkyl-carbonyl, $C_1$–$C_4$ alkylaminocarbonyl, di-($C_1$–$C_4$-alkyl)-amino-carbonyl, $C_1$–$C_4$-alkyl-carbonyloxy, $C_1$–$C_4$-alkyl-carbonylamino, $C_1$–$C_4$-alkoxy-carbonyloxy, $C_1$–$C_4$-alkoxy-carbonylamino, $C_1$–$C_4$-alkylamino-carbonyloxy or $C_1$–$C_4$-alkylamino-carbonylamino (each of which is optionally substituted by halogen or $C_1$–$C_4$-alkoxy), phenyl, phenoxy, phenylthio, phenylsulphinyl, phenylsulphonyl, phenylamino, phenylcarbonyl, phenylazo or phenylazoxy (each of which is optionally substituted as indicated above), and Q is oxygen or sulphur,
wherein a hydroxyarene or mercaptoarene of the formula

   Ar—Q—H   (II)

is reacted with chlorodifluoromethane ($ClCHF_2$) in the presence of an aqueous alkali metal hydroxide or alkaline earth metal hydroxide at a temperature between 20° C. and 120° C., the improvement which comprises carrying out the reaction in the presence of a phase-transfer catalyst selected from the group consisting of a tetrasubstituted ammonium salt and a phosphonium salt, and in the presence of a non-polar or moderately polar solvent selected from the group consisting of an aliphatic or alicyclic hydrocarbon, an aromatic hydrocarbon which is optionally substituted by chlorine, and a branched alkyl ether.

2. A process according to claim 1, in which

Ar is phenyl or naphthyl, each of which is optionally substituted by at least one member selected from the group consisting of fluorine, chlorine, bromine, nitro, cyano, carboxyl, carbamoyl, methyl, ethyl, n- or i-propyl (each of which is optionally substituted by fluorine, chlorine, cyano, carboxyl, hydroxyl, methoxy, ethoxy, methoxycarbonyl, ethoxycarbonyl or phenyl), methoxy, ethoxy, n- or i-propoxy (each of which is optionally substituted by fluorine, chlorine, cyano, carboxyl, hydroxyl, methoxy, ethoxy, methoxycarbonyl or ethoxycarbonyl), methylthio, ethylthio, methylsulphinyl, ethylsulphinyl, methylsulphonyl or ethylsulphonyl (each of which is optionally substituted by fluorine or chlorine), methylamino, ethylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acetyloxy, propionyloxy, acetylamino, propionylamino, methoxycarbonyloxy, ethoxycarbonyloxy, methoxycarbonylamino, ethoxycarbonylamino, methylaminocarbonyloxy, ethylaminocarbonyloxy, methylaminocarbonyl amino or ethylaminocarbonylamino (each of which is optionally substituted by fluorine, chlorine, methoxy or ethoxy), and phenyl, phenoxy, phenylthio, phenysulphinyl, phenylsulphonyl, phenylamino or phenylcarbonyl (each of which is optionally substituted as indicated above).

3. A process according to claim 1, wherein the temperature is from 40° to 110° C.

4. A process according to claim 1, wherein the temperature is from 60° to 100° C.

5. A process according to claim 2, wherein per mol of starting material of formula (II) there are employed 1 to 5 mols of chlorodifluoromethane ($ClCHF_2$), 1.5 to 2.5 molar equivalents of alkali metal hydroxide or alkaline earth metal hydroxide, and 1 to 10 mol % of phase-transfer catalyst.

6. A process according to claims 2, wherein per mol of starting material of formula (II) there are employed 1.5 to 2.5 mols of chlorodifluoromethane ($ClCHF_2$), 1 to 5 molar equivalents of alkali metal hydroxide or alkaline earth metal hydroxide, and 1 to 10 mol % of phase-transfer catalyst.

7. A process according claim 1, wherein the phase transfer catalyst is selected from the group consisting of tetrabutylammonium bromide, tetrabutylammonium chloride, tetraoctylammonium chloride, tetrabutylammonium hydrogen sulphate, methyl-triocylammonium chloride, hexadecyl-trimethylammonium chloride, hexadecyl-trimethylammonium bromide, benzyltrimethylammonium chloride, benzyl-triethylammonium chloride, benzyltriethylammonium hydroxide, benzyl-tributyl-ammonium chloride, benzyl-tributylammonium bromide, tetrabutylphosphoniumbromide, tetrabutylphosphonium chloride, tributyl-hexadecylphosphonium bromide, butyl-triphenylphosphonium chloride, ethyl-trioctylphosphonium bromide and tetraphenylphosphonium bromide.

8. A process according to claim 1, wherein the solvent is selected from the group consisting of pentane, hexane, heptane, octane (in each case straight-chain or branched), cyclohexane, methylcyclohexane, petroleum ether, benzine, ligroin, benzene, toluene, xylene (all the isomers), cumene, chlorobenzene, o-dichlorobenzene, diisopropyl ether, diisobutyl ether, methyl sec-butyl ether, methyl tert-butyl ether, methyl sec-pentyl ether and methyl tert-pentyl ether.

9. A process according to claim 1, wherein the catalyst is an alkali metal hydroxide.

10. A process according to claim 1, wherein the starting compound of the formula (II), the alkali metal hydroxide or alkaline earth metal hydroxide dissolved or dispersed in water, the non-polar or moderately polar .solvent and the phase-transfer catalyst are mixed together, and chlorodifluoromethane is then passed into the mixture at the reaction temperature with vigorous stirring until the reaction is complete.

11. A process according to claim 2, wherein the temperature is from 60° to 100° C. per mol of starting material of the formula (II) there are employed 1.5 to 2.5 mols of chlorodifluoromethane ($ClCHF_2$), 1 to 5 molar equivalents of alkali metal hydroxide or alkaline earth metal hydroxide, and 1 to 10 mol % of phase-transfer catalyst, the phase transfer catalyst is selected from the group consisting of tetabutylammonium bromide, tetrabutylammonium chloride, tetraoctylammonium chloride, tetrabutylammonium hydrogen sulphate, methyl-triocylammonium chloride, hexadecyltrimethylammonium chloride, hexadecyl-trimethylammonium bromide, benzyltrimethyl-ammonium chloride, benzyl-triethylammonium chloride, benzyl-trimethylammonium hydroxide, benzyltriethylammonium hydroxide, benzyl-tributyl-ammonium chloride, benzyl-tributylammonium bromide, tetrabutylphosphonium bromide, tetrabutylphosphonium chloride, tributyl-hexadecylphosphonium bromide, butyl-triphenylphosphonium chloride, ethyl-trioctylphosphonium bromide and tetraphenylphosphonium bromide, the catalyst is an alkali metal hydroxide, dissolved or dispersed in water, the non-polar or moderately polar solvent and the phase-transfer catalyst are mixed together, and chlorodifluoromethane is then passed into the mixture at the reaction temperature with vigorous stirring until the reaction is complete.

* * * * *